United States Patent [19]

Thomenius

[11] Patent Number: 4,572,202
[45] Date of Patent: Feb. 25, 1986

[54] METHOD AND APPARATUS FOR HIGH-SPEED ULTRASONIC IMAGING

[75] Inventor: Kai E. Thomenius, Green Lane, Pa.

[73] Assignee: Elscint Inc., Boston, Mass.

[21] Appl. No.: 551,711

[22] Filed: Nov. 14, 1983

[51] Int. Cl.⁴ .............................................. A61B 10/00
[52] U.S. Cl. .................................... 128/660; 128/661; 358/112
[58] Field of Search ...................... 367/7, 11; 128/660, 128/661; 73/620, 625–626; 358/112

[56] References Cited

U.S. PATENT DOCUMENTS

| | | | |
|---|---|---|---|
| 3,954,098 | 5/1976 | Dick et al. ........................ | 128/661 X |
| 3,974,826 | 8/1976 | Eggleton et al. .................... | 128/661 |
| 4,034,744 | 7/1977 | Goldberg ............................ | 128/660 |
| 4,070,905 | 1/1978 | Kossoff ............................ | 128/660 X |
| 4,106,492 | 8/1978 | Schuette et al. .................... | 128/661 |
| 4,271,842 | 6/1981 | Specht et al. ....................... | 128/661 |

*Primary Examiner*—Kyle L. Howell
*Assistant Examiner*—Francis J. Jaworski
*Attorney, Agent, or Firm*—Sandler & Greenblum

[57] ABSTRACT

A method and apparatus for high-speed ultrasonic imaging of very rapidly moving bodily structures. A transducer produces sequential data frames corresponding to sequential images of bodily cross-sections produced by periodically scanning a body with an ultrasound beam produced by the transducer. Reflected ultrasonic echo pulses are digitized and stored in a memory array in which each data frame is stored in a single segment of a plurality of memory segments which form the memory. The transducer periodically scans the body at a predetermined first rate, whereas the sequential display of the sequential data frames occurs at a second predetermined rate which is different from the first rate. The system permits acquisition of data at a rate which is greater than the perception rate of the human eye and display of the acquired data at a rate which can be visualized by a human observer. An electrocardiogram generates a first control signal for controlling the transducer scan rate and a second control signal for timing the data storage can be triggered to occur at a desired portion of a cardiac cycle, e.g., when an abnormal cardiac event occurs.

5 Claims, 2 Drawing Figures

METHOD AND APPARATUS FOR HIGH-SPEED ULTRASONIC IMAGING

TECHNICAL FIELD OF THE INVENTION

The present invention relates to ultrasonic imaging systems, and more particularly, to high-speed ultrasonic imaging of rapidly moving body structures such as cardiac sections.

BACKGROUND OF THE INVENTION

In general, the ultra-sound imaging technique uses the pulse-echo method. According to such method, pulses of ultrasonic energy are generated by a piezoelectric transducer, for example, made of lead zirconate-titanate ceramic. Each short pulse is focused to a narrow beam. This focused beam is transmitted through a suitable conducting medium, e.g., water, into the body of a patient. A portion of the ultrasonic energy is reflected back toward the transducer at interfaces between various different structures of the body due to mechanical impedance discontinuities at the interface. The transducer converts the reflected mechanical energy into electrical signals. The time of arrival of the returning reflected signals indicates the position within the body of the interface. In other words, the timed spacing between the reflected signals or echoes is proportional to the physical spacing of the respective reflecting interfaces within the body. The amplitude of the echo is a function of the characteristics of the structures forming the interface.

The image-representing electrical signals corresponding to the characteristics of the reflected mechanical energy are then displayed on a display device. One type of display is termed an "A-scan" continuous display on which the electrical signals representing the reflected echo pulses are applied to the vertical deflection plates of a conventional cathode ray tube. The output of a time base or sweep generator is applied to the horizontal deflection plates of the CRT. The pulse-echo process is continuously repeated in synchronism with the sweep to produce a continuous display. In the display, time is proportional to range, and the height of the vertical deflections is a function of the reflected echo strength.

Another type of display device commonly employed is termed a "B-scan" display. Such a display is comparable to a conventional television display. In such a system, the reflected echo signals modulate the brightness of the display at each point scanned. Strongly reflecting internal structures, such as hardened artery walls, appear brighter on the display than weakly reflecting structures. This grey scale produces a useful diagnostic tool. A plurality of scan lines can be produced by scanning the ultrasonic beam produced by the transducer, either by a mechanical sector scan or a phased-array radar sector scan, at a predetermined rate and in a predetermined direction across the surface of the patient. The plurality of scan lines so produced can be used to yield a display of a cross-sectional picture in the plane of the scan produced by the reflector-scanner, which scans mechanically over a desired angle.

A limitation on diagnostic methodologies based on cardiac ultrasound imaging or "echocardiology" arises from the inability of conventional systems to image very rapidly moving bodily structures. Examples of such structure are: the aortic valve opening, which has a duration of approximately 30 milliseconds in an adult human and less in children, vibrations in various cardiac structures arising from regurgitant flow, and pediatric heart motion.

In systems which use the above-described "A-scan" continuous display, in which the images are displayed on a CRT, the inability to visually perceive extremely fast events results from limitations of the human observer, whose eye cannot perceive such rapid changes in real time. Thus, although the CRT is capable of displaying images of fast moving structures, the technique fails because the human observer cannot keep up with image update rates beyond a given threshold.

In systems which use the above-described "B-scan" display, where the images are presented on a standard CRT television-type display, the effective frame rate or image update rate is limited by the conventional television frame rate. According to the American television standard, this rate is 30 frames per second; and, according to the European standard, it is 25 frames per second. Even if the reflected echo signals corresponding to rapidly moving structures are recorded on a videotape, playing the tape in slow motion will not provide a system capable of displaying images corresponding to a "real time" rate faster than the above-noted conventional rates because the videotape is limited in that it is adapted for use with devices which have an acquisition rate equal to that of a standard television camera. In other words, the real time acquisition rate is 30 frames per second, and the display merely reflects this acquisition rate, but in slow motion. Thus, in such systems, real time events occuring at a rate faster than 30 events per second are beyond the capacity of the system.

Due to the these considerations, conventional ultrasound systems limit their image acquisition modes such that they do not exceed 30 frames per second. Systems which exceed this acquisition rate are either limited by the television frame rate or by displays where higher frame rates cannot be appreciated.

It is, therefore, an object of the present invention to provide a new and improved method and apparatus for high-speed ultrasonic imaging, in which the above-described barriers to high-speed acquisition in the prior art systems are overcome.

SUMMARY OF THE INVENTION

According to the present invention, there is provided an ultrasonic apparatus for high-speed imaging of sections of a body by transmitting ultrasonic energy into the body and determining the characteristics of the ultrasonic energy reflected therefrom. The apparatus includes transducer means for periodically scanning the body at a first predetermined rate greater than 30 scans per second with a beam of periodic pulses of ultrasonic energy over a predetermined scan angle and for converting reflected ultrasonic echo pulses to image-representing electrical signals. Display means are provided for sequentially displaying the sequential data frames with a second predetermined rate which is different from the first rate at which the transducer periodically scans the body.

Storage means having a plurality of memory segments can be provided for storing sequential data frames corresponding to the image-representing electrical signals. The second predetermined period can be greater than the first predetermined period.

A timing circuit can be used to synchronize the readout of the sequential data frames from the storage means with the sequential display of the sequential display of the data frames on the display means at the second predetermined rate. A rate adjustment circuit can be employed to generate a signal for controlling the timing circuit to alter the second predetermined rate.

The first predetermined rate can be determined by a first control signal generated by an electrocardiogram, the first control signal corresponding to a part of a cardiac cycle of the patient. An electrocardiogram can be used to generate a second control signal for timing the storage of the sequential data frames in the memory segments of the storage means. The second control signal can be used to terminate the storage of the sequential data frames or to initiate the storage of the sequential data frames. Also, the second control signal can occur at an intermediate point of the storage of the sequential data frames. A single electrocardiogram can be used both to generate a first control signal to determine the first predetermined period and to generate a second control signal for timing the storage of the sequential data frames in the memory segments of the storage means.

Thus, according to the present invention, the transducer means can be, for example, a very high-speed transducer probe, capable of acquiring data at a rate of 75 frames per second or higher for display on, for example, a sector-shaped display of 15°. At an acquisition rate of 75 frames per second, the image update occurs every 13.3 milliseconds. This rate would permit imaging the typically 30 millisecond aortic valve opening with two or three images. The probe speed can be increased beyond 75 frames per second to provide further enhancement of the technique. Each time the transducer probe images the body, a frame of image data is produced thereby. By periodically scanning the body with a predetermined rate, the transducer thus produces sequential frames of image data. These sequential frames can be written into a storage device which contains a plurality of memory segments for storing sequential data frames. The storage means can be, for example, a 512×512×8 memory array, which is subdivided into 16 memory segments of 128×128×8 bits each, with a single data frame of image data being stored in each memory segment. The contents of the memory segments can then be displayed sequentially with a second predetermined rate, which is different from the first predetermined rate with which the data was acquired. Rather than fixing the rate at which the sequential data frames are displayed, this rate can alternatively be manually selectable or adjusted by a rate adjustment circuit, with the rate at which the data is displayed preferably being chosen such that the human eye will be capable of perceiving the events in real time.

Accordingly, for a frame rate of 75 frames per second, the 16 data frames representing the image updates stored in the storage means can be captured in 213.3 milliseconds. Because this is a small fraction of a typical cardiac cycle, electrocardiogram-derived triggering, i.e., triggering based on the trace produced on an electrocardiogram, can be used to trigger the image acquisition rate so that any part of the cardiac cycle can be studied with high temporal resolution.

According to the present invention, there is also provided a method for high-speed imaging of sections of a body using an ultrasonic apparatus which includes a transducer for directing a beam of ultra-sound pulses toward the body and for converting reflected ultrasound echo pulses to image-representing electrical signals, a memory array having a plurality of memory segments, and display means for displaying data corresponding to the image-representing electrical signals. The method includes acquiring sequential frames of image data with a first predetermined rate greater than thirty frames per second by periodically scanning a body section over a predetermined scan angle with a beam of periodic pulses of ultrasonic energy emitted by the transducer means, and sequentially displaying the stored frames with a second predetermined rate which is different from the first predetermined rate. The method can also include storing the sequential frames of image data in the memory segments, each frame being stored in a separate segment of the memory array. The second predetermined rate can be greater than the first predetermined rate. The read-out of the sequential frames of image data from the segmented memory array is synchronized with the display of the sequential frames of data on the display means. The sequential frames are acquired by periodically scanning a body section over a predetermined scan angle with a beam of periodic pulses of ultrasonic energy emitted by the transducer means. The first predetermined rate is triggered using a first control signal generated by an electrocardiogram, the control signal corresponding to a part of a cardiac cycle of a patient.

The storage of the sequential data frames in the memory segments of the storage means can be timed using a second control signal generated by an electrocardiogram. This second control signal can be used to terminate the storage of the sequential data frames or to initiate the storage of the sequential data frames. In addition, the second control signal can occur at an intermediate point of the storage of the sequential data frames. A single electrocardiogram can be used to generate both a first control signal for triggering the first predetermined rate and a second control signal for timing the storage of the sequential data frames in the memory segments of the storage means.

The first predetermined rate can be, for example, approximately 75 frames per second or faster to provide resolution capable of analyzing cardiac motion. The second predetermined rate can be, for example, approximately 30 frames per second to correspond to the image update rate of a conventional U.S. television monitor. The segmented memory array can be a 512×512×8 bit memory array divided into 16 memory segments, each segment being a 128×128×8 bit memory array, and each segment storing a sequential data frame. The stored sequential frames can be displayed on a CRT television display. The predetermined scan angle can be, for example, approximately 15°, and the stored sequential frames can be displayed on a CRT television display having a sector-shaped display screen covering, for example, approximately 15°.

BRIEF DESCRIPTION OF THE DRAWINGS

Embodiments of the present invention are shown in the accompanying drawings, wherein.

DETAILED DESCRIPTION OF THE INVENTION

Figures 1, 2:
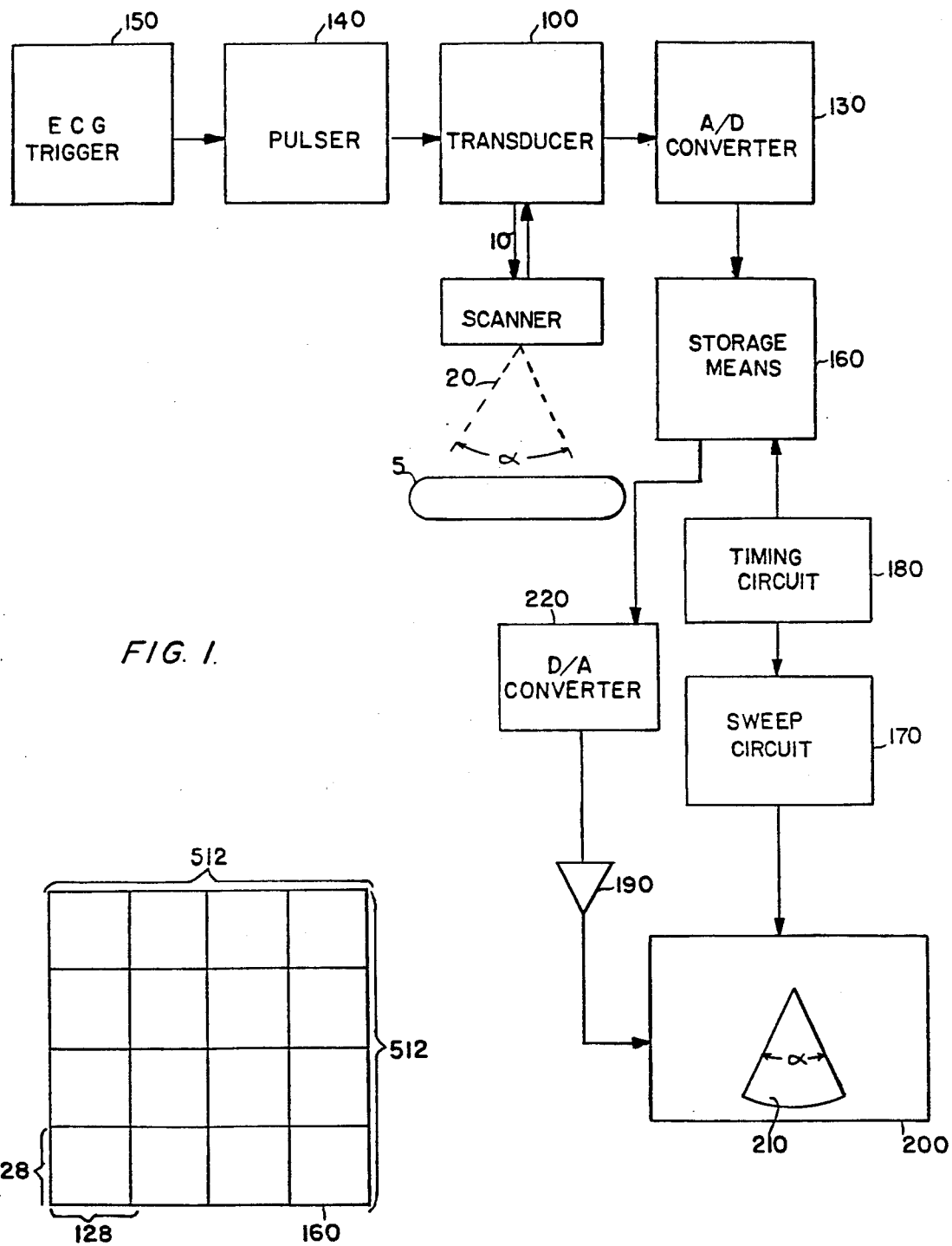
FIG. 1 is a schematic block diagram of an ultrasonic apparatus for high-speed ultrasonic imaging according to the present invention.
FIG. 2 is a diagram illustrating a segmented memory array for storing sequential data frames of image data according to the present invention.

Referring now to FIG. 1, reference numeral 5 represents a patient to be examined using transducer 100, which emits a beam 10 of ultrasonic energy. Scanner 110, which may be associated with either a mechanical sector scan system or a phased-array radar sector scan system, causes this beam to traverse a cross-section of patient 5 by periodically scanning through a sweep angle $\alpha$ across patient 5 with a predetermined scan rate $T_1$ which is determined by electrocardiogram trigger 150. Trigger 150 can alternatively be any other type of timing means, but according to the present description, electrocardiogram trigger 150 represents a trigger which is timed according to any desired cardiac cycle associated with the patient under examination.

Electrocardiogram trigger 150 generates a trigger signal which is coupled to scanner 110 to cause scanner 110 to scan patient 5 with beam 10 with scan period $T_1$ which is determined by a cardiac cycle which is of interest. Scanner 110 generates a control signal which is fed to pulser circuit 140, which produces an electrical pulse signal which is used to energize transducer 100. As noted above, transducer 100 can be, for example, a piezoelectric transducer, which, responsive to input electrical signals, generates an output of ultrasonic energy pulses.

Transducer 100 also functions in a "listening" mode by receiving the ultrasonic energy which is reflected back from the patient due to acoustic impedance discontinuities which exist at various structural interfaces within the body of patient 5. Transducer 100 receives such reflected mechanical ultrasonic energy and converts this into electrical signals which are coupled to analog-to-digital converter 130 which digitizes the data for storage in storage means 160.

The signals provided by transducer 100 to converter 130 constitute image-representing electrical signals, which correspond to periodic scans of a cross-section of the body. Each scan provides a data frame which represents an image of the body cross-section at the time of the scan. Thus, the periodic scanning of the patient produces sequential data frames, each data frame representing an image of the cross-section at a particular point in time. Analog-to-digital converter 130 converts the electrical signal output from transducer 100 into digital form for storage in storage means 160.

As illustrated in FIG. 2, storage means 160 is, according to one embodiment of the present invention, formed of a plurality of memory segments for storing the sequential data frames which correspond to the image-representing electrical signals generated by the transducer. In this embodiment, storage means 160 is a $512 \times 512 \times 8$ bit memory array divided into 16 memory segments, each segment being formed of a $128 \times 128 \times 8$ bit array. Each memory segment is used for storing single sequential data frames.

Electrocardiogram trigger 150 can also be used to generate a control signal for timing the storage of sequential data frames acquired by transducer 100 in the plurality of memory segments which form storage means 160. In other words, at a particular portion or point of interest of a cardiac cycle, the electrocardiogram can be used to generate a control signal which controls the timing of the storage of the sequential data frames. This data storage control signal from the electrocardiogram trigger circuit 150 can be fed along line 151 to analog-to-digital converter 130. As described below, this control signal can be used to initiate data storage, to terminate data storage or to indicate the timing of an intermediate point in data storage. In the case where the control signal is used to initiate storage, once the signal occurs, the succeeding n data frames acquired by the transducer which are necessary to fill the plurality of memory segments which form storage means 160 will be stored in storage means 160 for subsequent display on display unit 200. Of course, in the embodiment in which storage means 160 includes sixteen memory segments, the ECG timing signal initiates storage of the succeeding sixteen data frames acquired by the transducer. In the case in which the ECG control signal is used to terminate storage, this signal indicates that the present n data frames stored in storage means 160 are to be utilized for subsequent display on display means 200. Finally, in the embodiment in which the ECG control signal is used to trigger an intermediate point in the data storage cycle, once the timing signal occurs (assuming, e.g., the intermediate point is the mid-point of the storage cycle and the memory unit includes sixteen memory segments) the next eight data frames will be stored and the eight data frames which occurred immediately prior to the occurrence of the "mid-point" timing signal will be utilized and subsequently displayed on the display unit. It should be noted that where the electrocardiogram timing signal is used either to terminate data storage or mark an intermediate point of data storage, the data frames stored in the storage means will be constantly refreshed with data frames provided by the transducer via analog-to-digital converter 130, and the electrocardiogram control signal will signal either the endpoint of data storage or an intermediate point thereof. It should be noted further that in the case where the electrocardiogram control signal is used to initiate data storage, data storage need not begin until the control signal occurs. From a practical standpoint, the use of the electrocardiogram control signal to terminate data storage would be advantageous where, for example, it is desired to determine what happened prior to the occurance of an abnormal cardiac event with the objective being to determine what might have caused the abnormal cardiac event. Similarly, it might be desired to observe what happens subsequent to an abnormal cardiac event, in which case the electrocardiogram timing signal would be used to initiate data storage. Finally, it might be desired to observe what happened both prior to and subsequent to such abnormal event, in which case the control signal would be used to mark an intermediate point of data storage.

Referring again to FIG. 1, timing circuit 180 is used to synchronize the sequential read-out of the data stored in the memory segments within storage unit 160 with the display of this data with a predetermined display period $T_2$ on display unit 200. Rate adjustment circuit 230 is provided for generating a signal for controlling timing circuit 180 to alter the predetermined display rate $T_2$. The digital data from storage means 160 are converted to analog form by digital-to-analog converter 220 and are coupled through amplifier 190 to display 200, wherein the signals modulate the brightness of the scanning raster to obtain the desired cross-sectional image. Each scan line of display 200 represents a depth echo profile of the body for a particular angular orientation $\alpha$ of scanner 110. Reference numeral 210 illustrates a sector-shaped display screen covering an angle $\alpha$ corresponding to the scan angle of scanner 110.

Timing circuit 180 is also coupled to sweep circuit 170 which generates the signals to control the vertical and horizontal synchronization signals for display 200. For a two-dimensional "B-scan" display, the timing signals from timing circuit 180 synchronize the horizontal synchronization of the display such that the active portion of one scan line of the display corresponds to the data frame being currently read out from storage means 160. The second dimension of the desired cross-sectional image is obtained by synchronizing the vertical sweep rate of the display controlled by sweep circuit 170 with the time required for reading out an entire frame stored within a segment of storage means 160.

The operation of the system is as follows: Upon command from the electocardiogram trigger circuit 150, or other timing circuit, to scanner 110, scanner 110 generates a control signal which is fed to pulser circuit 140; pulser circuit 140 generates energizing pulses which excite transducer 100. This pulsing causes transducer 100 to emit a beam of periodic ultra-sound energy pulses which is reflected by scanner 110 into the body of patient 5. Responsive to a control signal generated by electrocardiogram trigger circuit 150, scanner 110 causes the ultra-sound beam 20 to scan through a sweep angle with a scan rate $T_1$ which may be determined by, e.g., the heart contraction rate. As noted above, trigger circuit 150 can alternatively be any other type of timing means which provides any desired scan period $T_1$. By scanning beam 20 through sweep angle $\alpha$, image data over a desired cross-section of patient 5 can be obtained. As beam 20 traverses the body, echo pulses are transmitted back toward transducer 100 due to acoustic impedance discontinuities at structural interfaces within body 5. As the ultra-sound echo pulses are received by transducer 100, the transducer functions to convert the received ultra-sound energy into electrical signals. These electrical signals are then processed by analog-to-digital converter 130 and stored in digital form in storage means 160.

Electrocardiogram trigger circuit 150 can also be used to generate a second control signal which is fed over line 151 to analog-to-digital converter 130 for timing the storage of sequential data frames acquired by the transducer in the plurality of memory segments forming storage means 160. In other words, at a particular point of interest of a cardiac cycle, the electrocardiogram can be used to generate a control signal which will control the timing of the storage of the sequential data frames. As described in full above, this control signal can be used to initiate storage, to terminate storage, or to signal an intermediate point in the data storage cycle.

Timing circuit 180 synchronizes the read-out of data from storage means 160 with the horizontal and vertical sweep rates of display 200., Timing circuit 180 controls the rate at which data frames are read sequentially from storage means 160 and also controls sweep circuit 170 which in turn controls the sweep rates of display means 200. The readout of data from storage means 160 is synchronized with the sweep rates of display 200 such that data frames are successively displayed on display 200 with a display period $T_2$ which can be different from the scan rate $T_2$ with which scanner 110 causes ultra-sound beam 20 to traverse sweep angle $\alpha$. Rate adjustment circuit 230 provides means by which rate $T_2$ can be altered by the generation of a signal for controlling timing circuit 180.

Storage means 160 can be divided into 16 subsegments of memory, as illustrated in FIG. 2, with a data frame being stored in each of these subsegments. The digital contents of the subsegments are read out sequentially and converted into analog form by digital-to-analog converter 220. The analog data so produced are coupled through amplifier 190 to display 200 in order to modulate the brightness of the scanning raster. Each scan line of the display represents a depth echo profile of body 5 for a particular angular orientation of scanner 110 through sweep angle $\alpha$. Display 200 includes a sector-shaped display screen 210 having an angle $\alpha$ corresponding to the sweep angle of scanner 110. Timing circuit 180 also operates to synchronize the vertical sweep rate of the display by sweep circuit 170 such that the read-out of the data contained in an entire data frame stored within a subsegment of storage means 160 corresponds to the frame update rate of display 200. Similarly, the read-out of a single horizontal line within a data frame stored in a subsegment corresponds to the horizontal sweep rate of display 200.

Accordingly, transducer 100 can be caused to periodically scan body 5 with a first predetermined rate responsive to the control pulses provided by electrocardiogram trigger circuit 150. The reflected ultrasonic echo pulses from body 5 are converted to image-representing electrical signals by transducer 100. These image-representing electrical signals are converted to digital form by analog-to-digital converter 130 and stored in storage means 160. Display means 200 is then utilized to sequentially display the sequential data frames stored in storage means 160 with a second predetermined rate which is different than the first predetermined rate with which the sequential data frames were acquired.

From the foregoing description, one skilled in the art can easily ascertain the essential characteristics of the present invention and, without departing from the spirit and the scope thereof, can make various changes and modifications of the invention to adapt it to various usages and conditions.

What is claimed is:

1. A method of high-speed ultrasonic imaging using an ultrasonic apparatus including a transducer for directing a beam of ultra-sound pulses toward a body and for converting reflective ultra-sound echo pulses to image-representing electrical signals, a memory array having a plurality of memory segments, and display means for displaying data corresponding to said image-representing electrical signals, comprising the steps of:
   (a) periodically scanning said body with said transducer at a rate of approximately 75 frames per second, thereby acquiring sequential frames of image data of a rapidly moving body structure whose display would be blurred were the frames acquired at the conventional rate of 30 frames per second;
   (b) storing the frames sequentially in different segments of said memory array; and
   (c) sequentially displaying said stored frames at a rate substantially less than the rate at which the frames were acquired, thereby enabling display of the acquired image data at a rate which can be visualized by a human observer.

2. The method as recited in claim 1 wherein said sequential frames are acquired by periodically scanning a said body section over a predetermined scan angle with a beam of periodic pulses of ultrasonic energy emitted by said transducer means.

3. The method as recited in claim 1 wherein the said rate at which display occurs is approximately 30 frames per second.

4. The method as recited in claim 1 wherein said segmented memory array comprises a 512×512×8 bit memory array divided into 16 of said memory segments, each segment comprising a 128×128×8 bit memory array, said storing step comprising storing each said sequential data frame in a respective said segment.

5. The method as recited in claim 1 including the further steps of monitoring a time-variable physiological parameter of said body, and triggering acquisition of said image data to acquire a window of image data of the rapidly moving structure of the body.

* * * * *